United States Patent [19]

Leeb et al.

[11] 4,034,603
[45] July 12, 1977

[54] METHOD OF AN APPARATUS FOR TESTING THE HARDNESS OF MATERIALS

[75] Inventors: Dietmar Leeb; Marco Brandestini, both of Zurich, Switzerland

[73] Assignee: Proceq SA, Zurich, Switzerland

[21] Appl. No.: 703,471

[22] Filed: July 9, 1976

Related U.S. Application Data

[63] Continuation of Ser. No. 628,252, Nov. 3, 1975, abandoned.

[30] Foreign Application Priority Data

Nov. 7, 1974  Germany .......................... 2452880

[51] Int. Cl.² ......................................... G01N 3/52
[52] U.S. Cl. ........................................ 73/79; 73/12
[58] Field of Search ........................... 73/79, 82, 12

[56] References Cited

U.S. PATENT DOCUMENTS

| | | | |
|---|---|---|---|
| 3,453,862 | 7/1969 | Elliott et al. ........................... | 73/12 |
| 3,538,743 | 11/1970 | Glidden ................................. | 73/12 |
| 3,879,982 | 4/1975 | Schmidt ................................. | 73/12 |

*Primary Examiner*—James J. Gill
*Assistant Examiner*—Anthony V. Ciarlante
*Attorney, Agent, or Firm*—Ladas, Parry, Von Gehr, Goldsmith & Deschamps

[57] ABSTRACT

A method of, and apparatus for, testing the hardness of a material by means of an impact device wherein an impact body having a test tip or point which is either integrated, e.g., connected with, or separate from, the impact body is brought to impact against the material to be tested. There is determined the velocity of the impact body and/or the test tip both directly before and after impact, and there is then formed a characteristic value from both velocities which is utilized as criterion for the hardness of the material.

28 Claims, 5 Drawing Figures

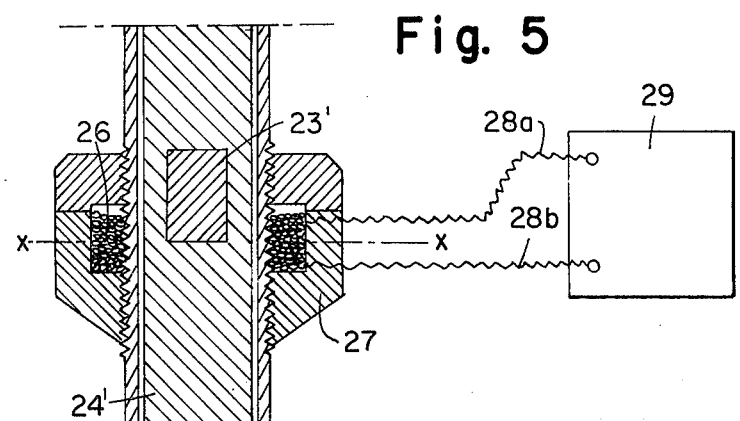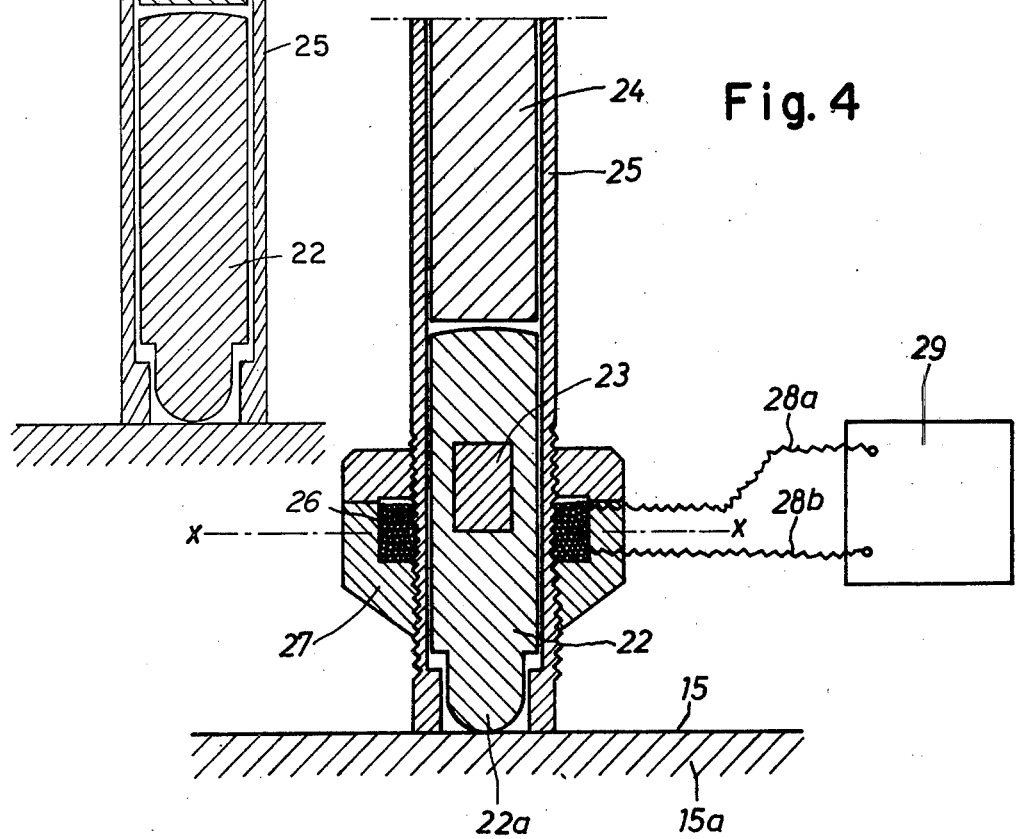

METHOD OF AN APPARATUS FOR TESTING THE HARDNESS OF MATERIALS

CROSS REFERENCE TO RELATED APPLICATION

This is a continuation of application Ser. No. 628,252 filed Nov. 3, 1975 and now abandoned.

BACKGROUND OF THE INVENTION

The present invention relates to a new and improved method of, and apparatus for, testing the hardness of a material, substance, stock or the like, generally simply referred to hereinafter as "material" or "materials."

The invention utilizes a hardness-test procedure wherein a test point or tip — the terms "test point" or "test tip" being broadly used herein to also denote any test portion or test element — is impacted against the material to be tested by means of a moved mass. The mass which is moved before impact, and which can possess a random geometry and can be formed of any suitable desired materials or substances, will be conveniently referred to in the following disclosure simply as "impact body" or "impact body member." The impact body and test tip can collectively form an integral or unitary component, or also can consist of separate parts movable relative to one another. For instance, the test tip or point can be constituted by a sphere or ball, a partially spherical pin or bolt, or a ball connected with a bolt or equivalent structure.

In order to determine the hardness of materials there have been utilized, apart from the heretofore known or so-called static indentation hardness procedures according to Brinell, Vickers and Rockwell, in many instances also dynamic hardness testing procedures. These rely upon the principle of bringing into contact with the material to be tested a test tip or point by impact or percussion thereof and, depending upon the technique employed, either the permanent deformation of the material, or the impact force between the test tip and the material, or the impact duration or else the potential residual energy of an impact body together with the test point after the rebound thereof from the material, constitutes a measure for the material hardness. However, the energy of the impact- or percussion action, for all of the dynamic testing procedures, always is selected to be so large that, due to the contact of the test tip or point at the material to be tested, there occur permanent deformations at such material.

SUMMARY OF THE INVENTION

Hence, it is a primary object of the present invention to provide a new and improved method of, and apparatus for, testing the hardness of materials in a manner not associated with the shortcomings and drawbacks of the prior art procedures.

A further object of the present invention aims at the provision of a new and improved method of, and apparatus for, hardness testing of a material according to a dynamic testing procedure, wherein there is particularly possible rapid performance of the hardness testing operation with small, compact, very simply constructed testing apparatuses or devices affording extremely accurate measurement results and without being dependent upon the direction of the impact.

A further important object of the present invention aims at a new and improved method of, and apparatus for, the dynamic hardness testing of a material in an extremely simple, efficient, accurate and rapid manner.

Yet a further object of this invention aims at novel apparatus for the hardness testing of materials, which apparatus is relatively simple in construction and design, extremely reliable in operation, provides for precise measurement results, is economical to manufacture and requires a minimum of maintenance and servicing.

Now in order to implement these and still further objects of the invention, which will become more readily apparent as the description proceeds, the novel method for hardness testing as comtemplated by the present invention, is manifested by the features that there is determined the velocity of an impact body member and/or its test tip or portion, moved by means of a random energy source, directly prior to and after impact with the material to be tested, and thereafter there is formed a characteristic value from both such velocities which is then utilized as criterion for the hardness of the material.

In the context of the present invention and the disclosure thereof as contained herein the velocity directly prior to impact is intended to mean the velocity which the impact body with the test point or tip, moved relative to the stationary material, then possesses prior to impact when it is located directly at the impact location or in its immediate vicinity or neighborhood. A more exact theoretical explanation of this concept is that it is the velocity of the impact body or impact body member at the moment of contact between the test point or tip and the material. In analogous manner the velocity directly after impact is defined as the velocity which the impact body with the test point, now moved in the opposite direction due to the resistance of the material, possesses after the rebound or bounce-back from the material to be tested when it is still directly located at the impact location or at the immediate vicinity or neighborhood thereof. Expressing this is a more theoretical manner, it is the velocity of the impact body or impact body member at the moment when the test tip or point or the like again lifts-off the material.

Depending upon the duration and the magnitude of the energy prior to impact which acts upon the impact body, it is possible for the impact body to possess the previously defined velocities to be determined as the measurement magnitudes, which velocities are also designated as impact velocity and rebound velocity, respectively, not only at the immediate neighborhood of the impact location, but also already at a slight spacing or even at a larger distance from such impact location. This is, for instance, then the case for the impact velocity when the impact body is not accelerated up to the impact location itself, rather is accelerated only up to a certain distance from such impact location, and thereafter, while permissibly neglecting the effect of the remaining forces, is moved further with a uniform velocity, i.e., the impact velocity, up to the impact location.

The inventive method is predicated upon an analysis of the known energy equation as defined below which, for instance, in the case of a spring or resilient impact device, for the residual energy remaining following impact, can be expressed as follows:

EQUATION 1

$$m \cdot v_R^2/2 = (c \cdot s_R^2/2) \pm mg \cdot s_R + E_R$$

In this Equation the indicated reference characters denote the following:

$m$ = mass of the impact body
$v_R$ = rebound velocity of the impact body
$c$ = spring constant
$s_R$ = rebound path of the impact body against the spring action (= part of the spring path)
$g$ = gravitational constant.

The value $m \cdot v_R^2/2$ constitutes the inertia or kinetic energy of the impact body at the start of rebound. Upon completion of such rebound this kinetic energy is transformed into the following energy components:

$c \cdot s_R^2/2$ = potential residual energy of the spring system.
$mg \cdot s_R$ = potential residual-gravitational energy. This energy component can be positive, negative, or null, depending upon the impact direction.
$E_R$ = the energy consumed due to frictional effects along the rebound path $s_R$.

In the case of rebound devices there is measured as the criterion for the hardness the rebound path $s_R$ i.e., the size of the path of the potential residual energy. According to Equation (1) this value is dependent upon the impact direction and the effect of the frictional forces along the rebound path. On the other hand, if there is measured as the criterion or measure for the residual energy a characteristic magnitude of the kinetic energy, namely the rebound velocity, then there are completely eliminated both of the path-dependent error effects.

However, both of these error effects also furthermore arise even when generating the impact energy itself, and specifically in the case of all dynamic hardness testing techniques, as demonstrated by the analogous energy equation for the impact energy prevailing prior to impact:

EQUATION 2

$$c \cdot s^2/2 + mgs + E = m \cdot v_A^2/2$$

In this Equation the indicated reference characters denote the following:

$m$ = mass of the impact body
$c$ = spring constant
$g$ = gravitational constant
$s$ = total spring path
$v_A$ = impact velocity of the impact body
$E$ = the energy component consumed by frictional effects along the entire spring path.

The value $m \cdot v_A^2/2$ constitutes the kinetic energy of the impact body member or impact body directly prior to impact. This energy is produced by transforming the potential energy of the spring system $c \cdot s^2/2$, wherein again the potential gravitational energy and the frictional forces along the spring path come into play as disturbance magnitudes. Since maintaining constant the impact energy at all spring impact devices used in dynamic hardness testing procedures occurs only by introducing constant values for the spring constant and spring path, the effective kinetic energy at the impact location itself therefore is not constant due to both error or disturbance effects.

If there is also measured in this case the impact velocity $v_A$ as a measure for the kinetic energy, then it however still contains both of the error effects in contrast to the rebound velocity. Therefore, however, according to the invention, following both velocity measurements both of the velocities are related to one another, in other words, as a characteristic value or characteristic for the hardness there is preferably formed the quotient $v_R/v_A$. Due to such quotient formation there are markedly reduced errors in the impact velocity, since namely with not too great changes in the impact velocity the rebound velocity in the first approximation also changes in proportion thereto. There also can be formed as equally useful hardness characteristic values from the measured velocity, for instance, also the functions $\sqrt{v_R/v_A}$ on $(v_R/v_A)^2$, the last-mentioned function being directly proportional to the change in the kinetic energy due to impact.

The error effect in the impact velocity, which is predicated upon the impact direction, can be preferably still further considerably reduced in that the impact body-mass and the velocity with which this mass is moved by means of a random energy source, can be mutually matched to one another such that the kinetic energy present at the impact body prior to impact is large in comparison to positive or negative energy components to which the impact body-mass is subjected to under the effect of gravity.

The apparatus of this development for the performance of the aforesaid method aspects is manifested by the features that the impact body member or test tip member is rigidly connected with the movable part or component of a transducer for converting the velocities, which at least one of said members possesses at the impact location, into proportional electrical signals. There can be employed as the transducer a moving-magnet or plunger-type magnet transmitter, the movable permanent magnet of which is connected with the impact body and the stationary coil or winding component of which is fixed to the impact body-guide or guide means, or another electromagnetic transmitter, the movable soft magnetic part or component of which is connected with the impact body and its stationary coil-permanent magnet-part or component is fixed to the impact body-guide.

The transducer component or portion which is rigidly fixed with the impact body-guide can be electrically conductively connected with a measurement device for the measurement and storage of the generated electrical signals which are proportional to the velocity, and furthermore, the measurement device can contain mechanism or means for the determination of the hardness characteristic values formed from such signals.

Due to the use of the disclosed transducer for generating velocity-porportional electrical signals, there is possible a contactless measurement of the instantaneous velocity of the impact body at practically optional proximity to the impact location. Since the signals can be electronically measured and further processed, the measurement results, apart from the extreme accuracy which can be thusly obtained, further provide the advantage that they are available in digital form directly following the measurement operation.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 4 is a longitudinal sectional view through the forward part or portion of a hardness testing apparatus illustrating a separate arrangement of the impact body and testing tip or point; and FIG. 5 shows a view similar to FIG. 4 of a further form of hardness testing apparatus.

DETAILED DESCRIPTION OF THE PREFERRED EMBODIMENTS

Figure 1:
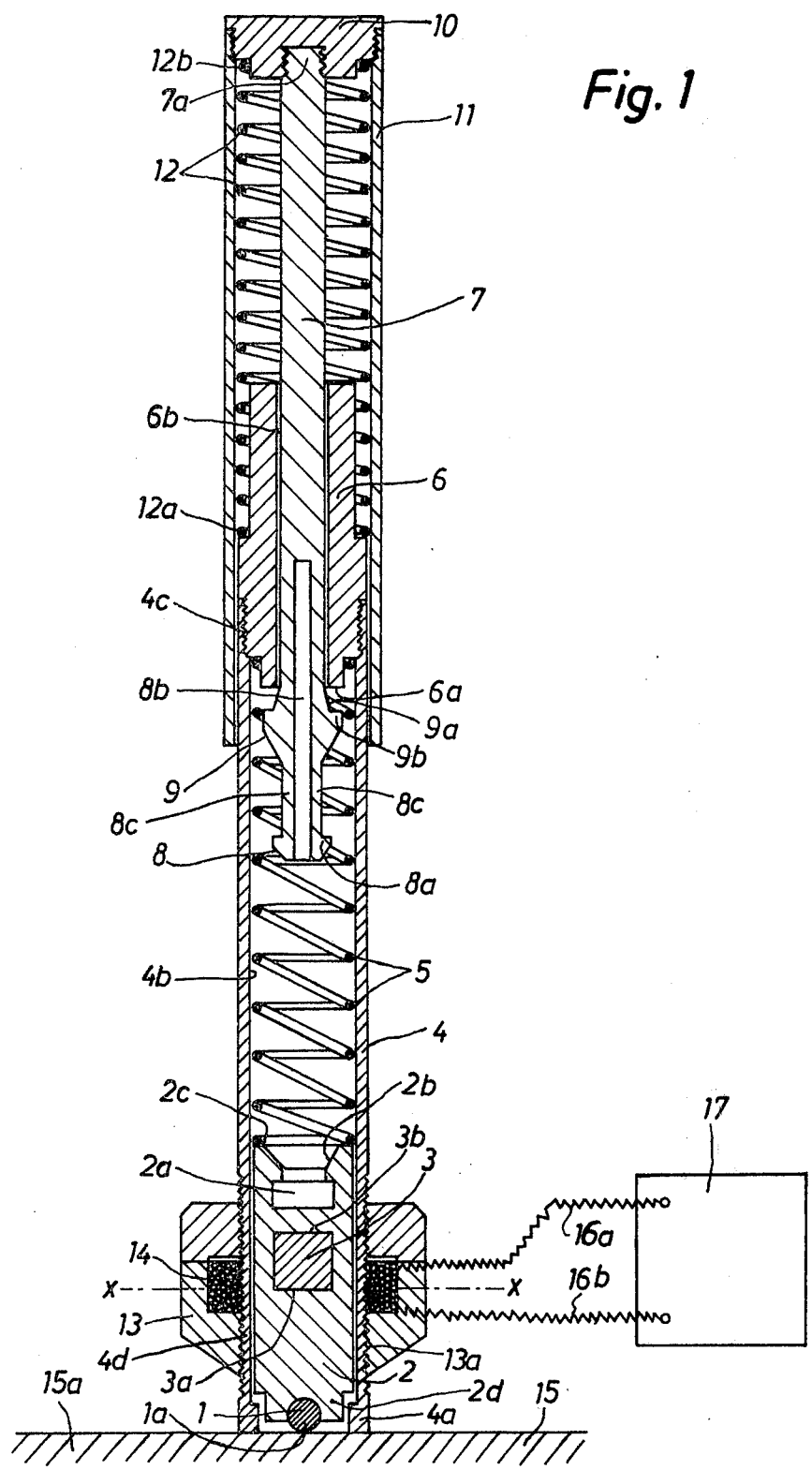
FIG. 1 is a longitudinal sectional view through a hardness testing apparatus constructed according to the teachings of the present invention and useful for carrying out the method aspects thereof.

Describing now the drawings, it is to be understood that in conjunction therewith there will be described, by way of example and not limitation, preferred exemplary embodiments of aparatus for testing the hardness of materials and useful in the practice of the method aspects of this development. The hardness testing apparatus as shown in FIG. 1 will be seen to comprise a forward or front substantially tubular-like housing 4 having an open front end 4a which, during testing, is placed upon a surface 15 of the material 15a to be tested or checked. Within the housing 4, the inner surface 4b of which forms a guide or guide means, there is mounted for lengthwise displacement or movement an impact body or impact body member 2 and a helical compression spring 5 or equivalent structure. The substantially cylindrically constructed impact body 2 is fixedly connected, on the one hand, at its front end 2d with a testing point or tip 1 or equivalent structure and, on the other hand, guides in rigid connection therewith a substantially cylindrical permanent magnet 3 having an axial arrangement of the poles 3a and 3b, as shown. The testing or test tip 1, in the illustrated exemplary embodiment, is constituted by way of example as a sphere or ball 1a formed of hardened steel or another suitable hard material possessing properties enabling it to indent or impress into the material 15a the hardness of which is to be tested or measured.

At its rear end 2c the impact body 2 contains an axially extending cylindrical bore 2a serving for the releasable reception of a resilient tip or front portion 8 of a lengthwise extending holding rod or member 7 for the impact body 2. This tip or front portion 8 of the rod 7 can be introduced through the conical portion 2b into the bore 2a. The compression spring 5, which has been illustrated in FIG. 1 in its relaxed or unloaded condition, serves to produce the impact energy which must be of such a magnitude that after penetration of the testing point or tip 1 into the material 15a to be tested there is permanent deformation of such material. The force of the spring 5 is applied to the impact body 2 at its rear end or surface 2c. The housing 4 is connected at its rear end 4c with a guide bushing or sleeve 6 in the bore 6b of which there is mounted for lengthwise displacement the holding rod or member 7. The rear end 7a of the rod 7 — which defines a type of clamp as will be explained more fully hereinafter — is fixedly connected by means of a cap or cap member 10 with a rear or rearward substantially tubular-housing 11 which, in turn, is displaceably mounted for lengthwise movement upon the front housing 4. The forward end or region of the tip or front portion 8, which is constructed to be radially resilient by the provision of crosswise arranged longitudinal or lengthwise extending slots, such as the slot 8b visible in FIG. 1, and forming the resilient depending arms or fingers 8c, includes the special elements constituted by the rod tip or front portion 8 and the release means 9.

As mentioned the rod tip 8 comprises four resilient pieces or depending fingers 8c embodying substantially conically forwardly tapering shoulders 8a which, following movement of the rod tip 8 into the cylindrical bore or recess 2a, serve as entrainment means for the impact body or impact body member 2. The release means or mechanism 9 comprises the abutment cone 9a and the terminal or end stop 9b. The function of the abutment cone 9a or equivalent means is that, upon retraction of the rod or clamp-like member 7, the resilient fingers or arms 8c are compressed together in such a manner that the rod tip or front portion 8 again releases the entrained impact body 2. The terminal or end stop 9b serves to limit the return movement or rearward path of the rod or clamp-like member 7 and which terminal stop, for this purpose, bears upon end face 6a of the guide bushing or sleeve 6. In the rear housing 11 there is arranged a further helical compression spring 12 or equivalent structure which is under permanent tension, the ends 12a and 12b of which bear upon the guide bushing 6 and the cap 10, respectively, and continually rearwardly biases or presses the rod 7 connected with such cap 10 until its end or terminal stop 9b contacts the end face 6a. The pre-bias or pre-stress of the spring 12 at least is as large as the spring force of the front spring 5, inclusive of the resistance of the abutment cone 9a.

Continuing, it will be recognized that at the outside 4d of the front housing 4 a coil or winding 14 located in a holder 13 is arranged such that the coil axis $x-x$ then approximately coincides with the front end 3a of permanent magnet 3 when the body 2 just strikes or impacts the material 15a. For the exact adjustment of the winding or coil axis $x-x$ relative to the front pole end 3a the bipartite constructed holder 13 can be displaced, for instance, by means of threading 13a along the front housing 4. The winding 14 is connected via the lines or conductors 16a, 16b with a suitable measurement- and indicator device 17.

Figure 2:
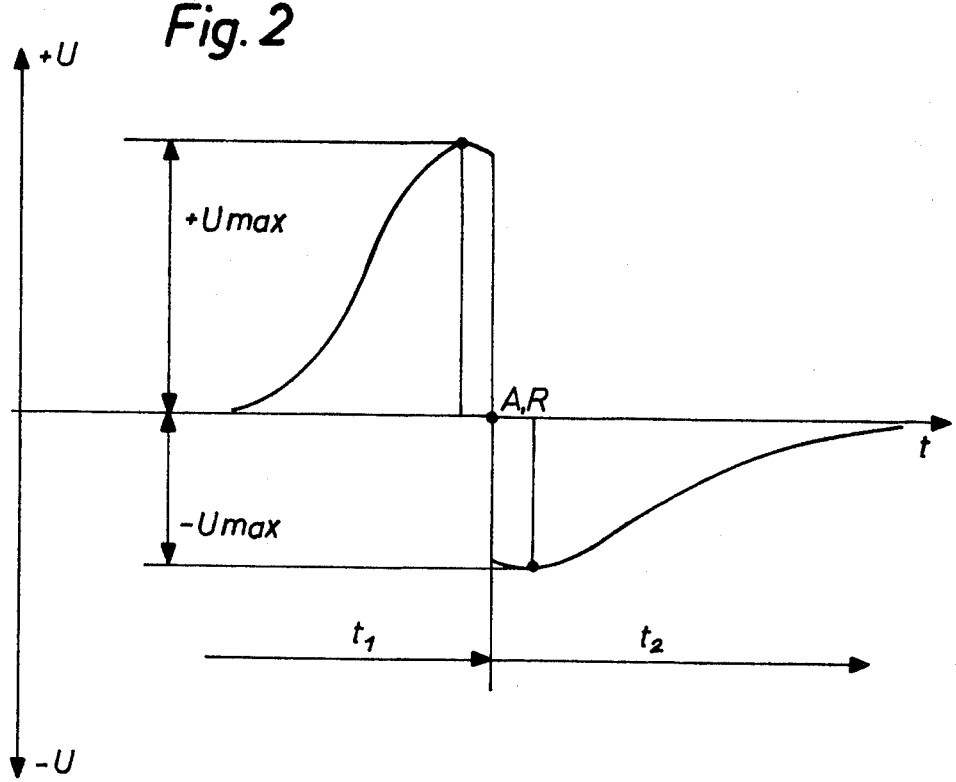
FIG. 2 is a graph of a typical output signal at the transducer.

FIG. 2 graphically illustrates a typical course of the voltage U generated in the transducer means 3, 14, these voltage being produced by the immersion of the movably entrained permanent magnet 3 arranged in the impact body 2 into the region of the winding or coil means 14 and the retraction of such permanent magnet 3 out of such winding means 14. The voltage course or envelope has been illustrated as a function of time $t$ for the sake of simplicity, wherein the time interval $t_1$ represents the approach of the impact body 2 at the impact location and the time interval $t_2$ the rebound phase. The time or time interval between impact and rebound itself, i.e., the actual duration of impact, is so small in elation to the time intervals $t_1$ and $t_2$ that such impact and rebound phenomena which have been designated in FIG. 2 by reference characters A, R can be portrayed and considered as simultaneously occurring. The maximum values $+U_{max}$, $-U_{max}$ occur as a function of a predetermined mutual position between the winding or coil axis $x-x$ and the magnet end 3a and are directly proportional to the velocity of the impact body 2 which prevails at such location and rigidly connected with the magnet 3. In FIG. 2 these maximum values occur shortly prior to impact and after rebound, respectively, i.e., the impact body is then located at the direct or immediate neighborhood of the impact location at which time its velocity is transformed into the electrical potential or voltage proportional thereto. The adjustment of the winding or winding means 14, which is displaceable upon the housing 4 also can be, however, chosen such that the occurrence of the maximum values coincide with the impact phenomena designated by reference characters A, R in FIG. 2, which means that the velocity of the impact body is measured directly upon impact and rebound, respectively.

Figure 3:
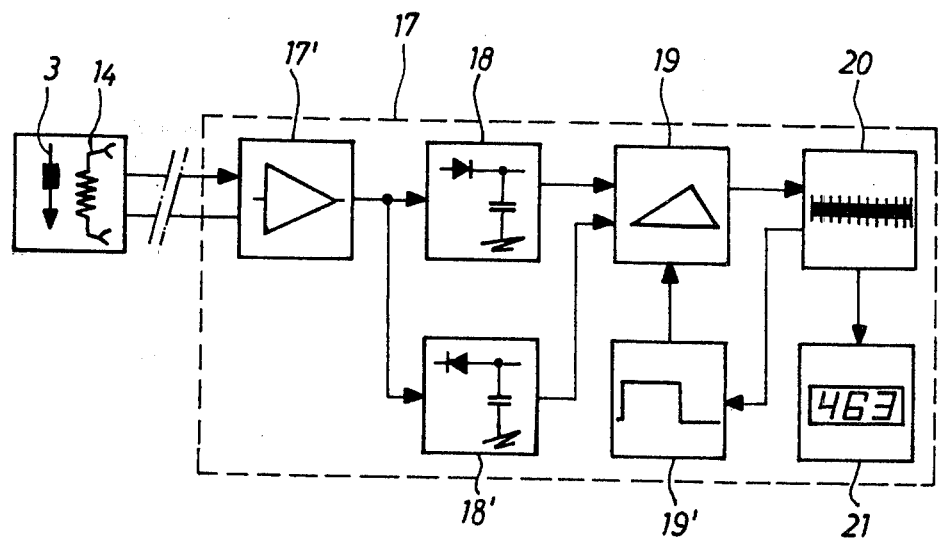
FIG. 3 is an electrical block circuit diagram of a measurement- and indicator device used in conjunction with the evaluation of the transducer signal.

The electrical block circuit diagram of the measurement- and indicator device 17 illustrated by way of example in FIG. 3 will be understood to encompass an amplifier 17', two peak storages or stores 18, 18', the storage magnitudes of which are delivered as input magnitudes or values to a double-slope analog-digital converter 19 which is controlled by a control component or control means 19', where there is formed the digital quotient from the rebound velocity and the forward velocity, and which is then indicated by means of a counter 20 and the indicator 21.

Having had the benefit of the above discussion of the exemplary embodiment of apparatus, there now will be considered the function of such hardness testing apparatus which is as follows:

During the determination of the hardness of a sample or piece of material 15a the front end 4a of housing 4 is vertically placed upon the surface 15 of the material 15a to be tested, i.e., in this case the above-mentioned sample, and the apparatus is held with one hand at the holder 13 while with the other hand the rear housing 11 and the rod or clamp-type member 7 fixedly connected therewith is pressed via the cap member 10 towards the material until penetration of the rod tip 8 into the bore 2a of the impact body 2. During the rearward movement of the rod 7, which takes place under the action of the pre-biased or pre-stressed spring 12 by simply releasing the contact pressure at the rear housing 11, the impact body 2 is entrained and thus stresses or loads the spring 5. The further occurring rearward movement, upon penetration of the abutment cone 9a into the bore 6a of the guide bushing or sleeve 6, results in a compression or pressing together of the rod tip 8, thereby releasing the impact body 2 which then impacts against the material 15a to be tested under the action of the pre-biased or loaded spring 5. The velocities which are reached by the impact body 2 directly prior to and after impact are converted, in the already described manner, into the electrical voltages or potentials which are proportional thereto, and which voltages are measured and further processed by means of the measurement and indicator device or apparatus 17 illustrated in FIG. 3.

The quotient of both velocities which is preferably formed as the criterion for the material hardness is always smaller than 1, and varies for instance between 0.300 and 0.800 for the group of materials composed of steel for a predetermined combination of testing tip-type and impact energy.

The apparatus for the performance of the method aspects of this invention of course also can be constructed differently than disclosed for the heretofore considered exemplary embodiment. Thus, for instance, depending upon the field of application, the impact energy also can be produced by the force of gravity or by the electromagnetic field of a solenoid, and as the elements for the velocity measurement there can be used, for instance, double light barriers or photocells which are operatively connected with a time measuring device. Also by way of completeness it is mentioned that conventional techniques, such as casting, bonding, molding and so forth can be employed to fixedly connect the permanent magnet or equivalent structure in the impact body member or tip member, as the case may be.

The preferred exemplary embodiment of impact body constitutes a construction wherein the impact body and testing tip member collectively form a unitary or single component — sometimes referred to herein as an integral or integrated component. However, it is also readily possible to construct the impact device in such a way that the impact body and the testing tip or point or equivalent structure form separate components, wherein only the impact body is moved and the testing point or tip bears against the material to be tested. With such an arrangement of impact body and testing tip the hardness testing method can be carried out by measuring the velocity in two different ways. According to a first technique the method is characterized by the feature of measuring the velocity of the impact body directly prior to its impact and directly after its rebound from the testing point or tip which bears against the material to be tested. The method according to the second technique is characterized by measuring the maximum velocity which prevails at the testing point or tip directly after impact of the impact body, i.e., at the start of its penetration into the material to be tested, and by measuring the maximum velocity which such component possesses after its rebound from the material to be tested. In contrast to measuring the velocity of the impact body in accordance with the first technique, the maximum velocities to be measured according to the second technique arise by virtue of the acceleration of the testing tip which takes place along a very small distance or path.

The exemplary embodiment illustrated in FIG. 4 shows a separate i.e., disconnected arrangement of the impact body or impact body member 24 and the testing point or tip member 22 or equivalent structure for measuring the maximum velocities of the testing point or tip 22. With this embodiment a permanent magnet 23 is mounted in the testing point or tip 32. Furthermore, in this case the testing point or tip 22 consists of a bolt formed of e.g. hardened steel with a substantially spherical-shaped, ground front portion 22a. The impact body 24 likewise possesses, for instance, a cylindrical cross-section and, just as was the case for the testing point or tip 22, is mounted to be lengthwise displaceable in the tubular-like housing 25. The mass of the impact body 24 can be the same or also greater than that of the testing point or tip 22. The rear end of the impact body 24, which has not been particularly illustrated in FIG. 4, likewise can be constructed like the entire apparatus for generating the impact as has already been illustrated and disclosed in conjunction with FIG. 1. In analogous manner, as in FIG. 1 the coil or winding means 26 located in the holder 27 of the arrangement of FIG. 4 can be connected via the conductors or lines 28a and 28b with the measurement- and indicator device 29. The mode of operation of this embodiment will be readily apparent from the previous discussion and thus need not be further considered.

In the apparatus shown in FIG. 5, the velocity of the impact body member 24' is measured immediately before impact with the tip member 22 and immediately after rebound therefrom, by using the same measuring device 26–29 as in FIG. 4, but arranged near the permanent magnet 23' mounted in the impact body 24'.

While there is shown and described present preferred embodiments of the invention, it is to be distinctly understood that the invention is not limited thereto, but may be otherwise variously embodied and practiced within the scope of the following claims.

Accordingly, what is claimed is:

1. A method of testing the hardness of a material by means of an impact device, comprising the steps of:
   a. providing an impact body member and a separate test member having a test tip;
   b. providing means for driving said impact body member to engage said test member;
   c. employing said driving means to drive the impact body member towards the material to be tested and to engage the test member thereby causing the test tip to impact said material and the test member to rebound therefrom;
   d. determining the velocity of at least one of said members immediately prior to impact;
   e. determining the velocity of at least one of said members immediately after impact; and
   f. forming a measure of the hardness of the material from said velocities.

2. A method as claimed in claim 1, wherein steps (d) and (e) comprise determining the velocity of said impact body member immediately prior to impact and immediately after impact.

3. A method as claimed in claim 1, wherein steps (d) and (e) comprise determining the velocity of said test member immediately prior to impact and immediately after impact.

4. A method as claimed in claim 1, wherein step (d) comprises determining the velocity of said test member immediately prior to impact.

5. A method as claimed in claim 1, wherein step (d) comprises determining the velocity of said impact body member immediately prior to impact.

6. A method as claimed in claim 1, wherein step (e) comprises determining the velocity of said test member immediately after impact.

7. A method as claimed in claim 1, wherein step (e) comprises determining the velocity of said impact body member immediately after impact.

8. A method as claimed in claim 1, wherein prior to step (c) said test member bears freely against the material to be tested, and steps (d) and (e) comprise determining the velocity of said impact body member immediately prior to impact with the test member and immediately after rebound therefrom.

9. A method as claimed in claim 1, wherein prior to step (c) the test member bears freely against the material to be tested and steps (d) and (e) comprise determining the maximum velocity of the test member after being struck by the impact body member and the maximum velocity of the test member on rebound from the material to be tested.

10. A method as claimed in claim 1, wherein step (f) comprises forming the quotient of the two velocities.

11. A method as claimed in claim 1, including the step of forming the square of the quotient of the two velocities.

12. A method of testing the hardness of a material by means of an impact device, comprising the steps of:
   a. providing an impact body member having a test tip integral therewith;
   b. providing means for driving said impact body member towards the material to be tested;
   c. employing said driving means to drive the impact body member towards the material to be tested so that the test tip impacts said material and the impact body member rebounds therefrom;
   d. determining the velocity of said impact body member immediately prior to impact and immediately after impact; and
   e. forming a measure of the hardness of the material from said velocities.

13. A method as claimed in claim 12, wherein step (e) comprises forming the quotient of the two velocities.

14. A method as claimed in claim 12, wherein step (e) comprises forming the square of the quotient of the two velocities.

15. An apparatus for testing the hardness of a material, comprising an impact body member, a separate test member having a test tip, means for driving said impact body member to engage said test member and thereby cause the test tip to impact the material to be tested, and transducer means comprising a first element fixedly connected to one of said members and a second element relative to which said one member moves said transducer mans being capable of detecting the velocity of said one member immediately prior and immediately after impact of the test tip with the material to be tested and of generating therefrom electrical signals approximately proportional to these velocities and means for forming a measure of hardness of the material from said electrical signals.

16. An apparatus as claimed in claim 15, wherein said first element is fixedly connected with said impact body member.

17. An apparatus as claimed in claim 15, wherein said first element is fixedly connected with said test member.

18. An apparatus as claimed in claim 15, further comprising guide means for guiding movement of said impact body member, and wherein said first element comprises magnetic material and said second element comprises a winding secured to said guide means.

19. An apparatus as claimed in claim 18, wherein said first element comprises permanent magnet material.

20. An apparatus as claimed in claim 18, further comprising circuit means for measuring, storing and processing electrical signals, said circuit means being connected to receive electrical signals generated in said winding.

21. An apparatus as claimed in claim 15, wherein the mass of the impact body member and the velocity with which such mass can be moved by the driving means are matched to one another such that the kinetic energy of the impact body member prior to impact is large in comparison to changes in energy of the impact body member due to gravitational effects.

22. An apparatus as claimed in claim 15, further comprising circuit means connected with said transducer means for receiving electrical signals generated thereby and detecting maximum values of said electrical signals and for directly forming a digital display of a quotient value formed from such signals.

23. An apparatus for testing the hardness of a material, comprising an impact body member having a test tip integral therewith, means for driving said impact body member thereby to cause the test tip to impact the material to be tested, and transducer means comprising a first element fixedly connected to said impact body member and a second element relative to which said impact body member moves, said transducer means being capable of detecting the velocity of said member immediately prior and immediately after impact of the test tip with the material to be tested and of generating therefrom electrical signals approximately proportional to these velocities and means for forming a measure of hardness of the material from said electrical signals.

24. An apparatus as claimed in claim 23, further comprising guide means for said impact body member, and wherein said first element comprises magnetic material and said second element comprises a winding secured to said guide means.

25. An apparatus as claimed in claim 24, wherein said magnetic material is permanent magnet material.

26. An apparatus as claimed in claim 24, further comprising circuit means for measuring, storing and processing electrical signals, said circuit means being connected with the winding means to receive electrical signals generated therein.

27. An apparatus as claimed in claim 23, wherein the mass of the impact body member and the velocity with which such mass is moved by the driving means are matched to one another such that the kinetic energy of the impact body member prior to impact in large in comparison to changes in the energy of the impact body member due to gravitational effects.

28. An apparatus as claimed in claim 23, further comprising circuit means connected to said transducer means for electronically detecting maximum values of the electrical signals generated by the transducer means, and for forming directly a digital display of a quotient value formed from such signals.

* * * * *